US00PP37291P2

(12) United States Plant Patent
Miner et al.

(10) Patent No.: US PP37,291 P2
(45) Date of Patent: Mar. 3, 2026

(54) ***EUPHORBIA* PLANT NAMED 'Miner's Berry Bordeaux'**

(50) Latin Name: ***Euphorbia* hybrid**
Varietal Denomination: Miner's Berry Bordeaux

(71) Applicants: Keith Miner, Reno, NV (US); Jennifer Miner, Reno, NV (US)

(72) Inventors: Keith Miner, Reno, NV (US); Jennifer Miner, Reno, NV (US)

( * ) Notice: Subject to any disclaimer, the term of this patent is extended or adjusted under 35 U.S.C. 154(b) by 0 days.

(21) Appl. No.: 19/314,145

(22) Filed: Aug. 29, 2025

(51) Int. Cl.
*A01H 5/02* (2018.01)
*A01H 6/38* (2018.01)

(52) U.S. Cl.
USPC ..... Plt./302
CPC ..... *A01H 6/385* (2018.05)

(58) Field of Classification Search
USPC ..... Plt./302
CPC ..... A01H 5/02
See application file for complete search history.

*Primary Examiner* — Kent L Bell
(74) *Attorney, Agent, or Firm* — Penny J. Aguirre

(57) ABSTRACT

A new cultivar of *Euphorbia* plant named 'Miner's Berry Bordeaux' that is characterized by its new foliage and stems that are very dark burgundy red in color maintaining the color throughout the season with the foliage changing to dark rose pink in the fall before the plant goes dormant, its upright compact plant habit, its clusters of unique dark burgundy involucre bracts surrounding tiny yellow-green floral bracts, its cold hardiness at least to U.S.D.A. Zone 4, and its high resistance to deer.

3 Drawing Sheets

Botanical classification: *Euphorbia* hybrid.
Varietal denomination: 'Miner's Berry Bordeaux'.

BACKGROUND OF THE INVENTION

The present invention relates to a new and distinct cultivar of *Euphorbia* of hybrid origin and will be referred to hereafter by its cultivar name, 'Miner's Berry Bordeaux'. 'Miner's Berry Bordeaux' represents a new herbaceous perennial grown for landscape and container use.

The new cultivar was discovered as a chance seedling by the Inventors in June of 2023 growing outdoors in a container in Foresthill, California. The parents of the new cultivar are unknown, however *Euphorbia* 'Cherokee' (not patented) is thought to be the possible parent based on it's proximity to the discovered seedling and the characteristics of the new cultivar.

Asexual propagation of the new cultivar was first accomplished by stem cuttings by the Inventor in September of 2023 in Foresthill, California. Asexual propagation by stem cuttings has shown that the characteristics of the new cultivar are stable and are reproduced true to type in successive generations.

SUMMARY OF THE INVENTION

The following traits have been repeatedly observed and represent the characteristics of the new cultivar. These attributes in combination distinguish 'Miner's Berry Bordeaux' as a new and unique cultivar of *Euphorbia*.

1. 'Miner's Berry Bordeaux' exhibits new foliage and stems that are very dark burgundy red in color maintaining the color throughout the season with the foliage changing to dark rose pink in the fall before the plant goes dormant.

2. 'Miner's Berry Bordeaux' exhibits a upright compact plant habit.
3. 'Miner's Berry Bordeaux' exhibits clusters of unique dark burgundy involucre bracts surrounding tiny yellow-green floral bracts.
4. 'Miner's Berry Bordeaux' exhibits cold hardiness at least to U.S.D.A. Zone 4.
5. 'Miner's Berry Bordeaux' exhibits high resistance to deer.

The probable parent plant of 'Miner's Berry Bordeaux', 'Cherokee', is similar to 'Miner's Berry Bordeaux' in having burgundy foliage but differs from 'Miner's Berry Bordeaux' in having foliage that turns green in color in summer, a slightly smaller plant size, and shorter stems. 'Miner's Berry Bordeaux' can also be compared to the *Euphorbia dulcis* cultivar 'Chameleon' (not patented). 'Chameleon' is similar to 'Miner's Berry Bordeaux' in having high deer resistance and burgundy colored bracts and foliage. 'Chameleon' differs from 'Miner's Berry Bordeaux' in having young foliage that emerges grey-purple in spring, matures to a rich burgundy-purple-green color by summer, and a deeper purple with red tinges in autumn, green-yellow involucre bracts, a smaller plant size, and hardiness only to U.S.D.A. Zone 5.

STATEMENT REGARDING PRIOR DISCLOSURES BY THE INVENTORS

The Applicants assert that no publications or advertisements relating to sales, offers for sale, or public distribution occurred more than one year prior to the effective filing date of this application. Any information about the claimed plant would have been obtained from a direct or indirect disclosure from the Inventor. The Applicants claim a prior art exemption under 35 U.S.C. 102(b)(1) for disclosures and/or sales that fall within a one-year grace period prior to the filing date. Disclosures include website listings by Nursery Guide, Lawn & Garden Retailer, Flipping Book, PP&L, and Instagram.

BRIEF DESCRIPTION OF THE DRAWINGS

The accompanying colored photographs illustrate the overall appearance and distinct characteristics of the new *Euphorbia*. The photographs were taken of a plant 9-months in age as grown in Foresthill, California.

Figure 1:
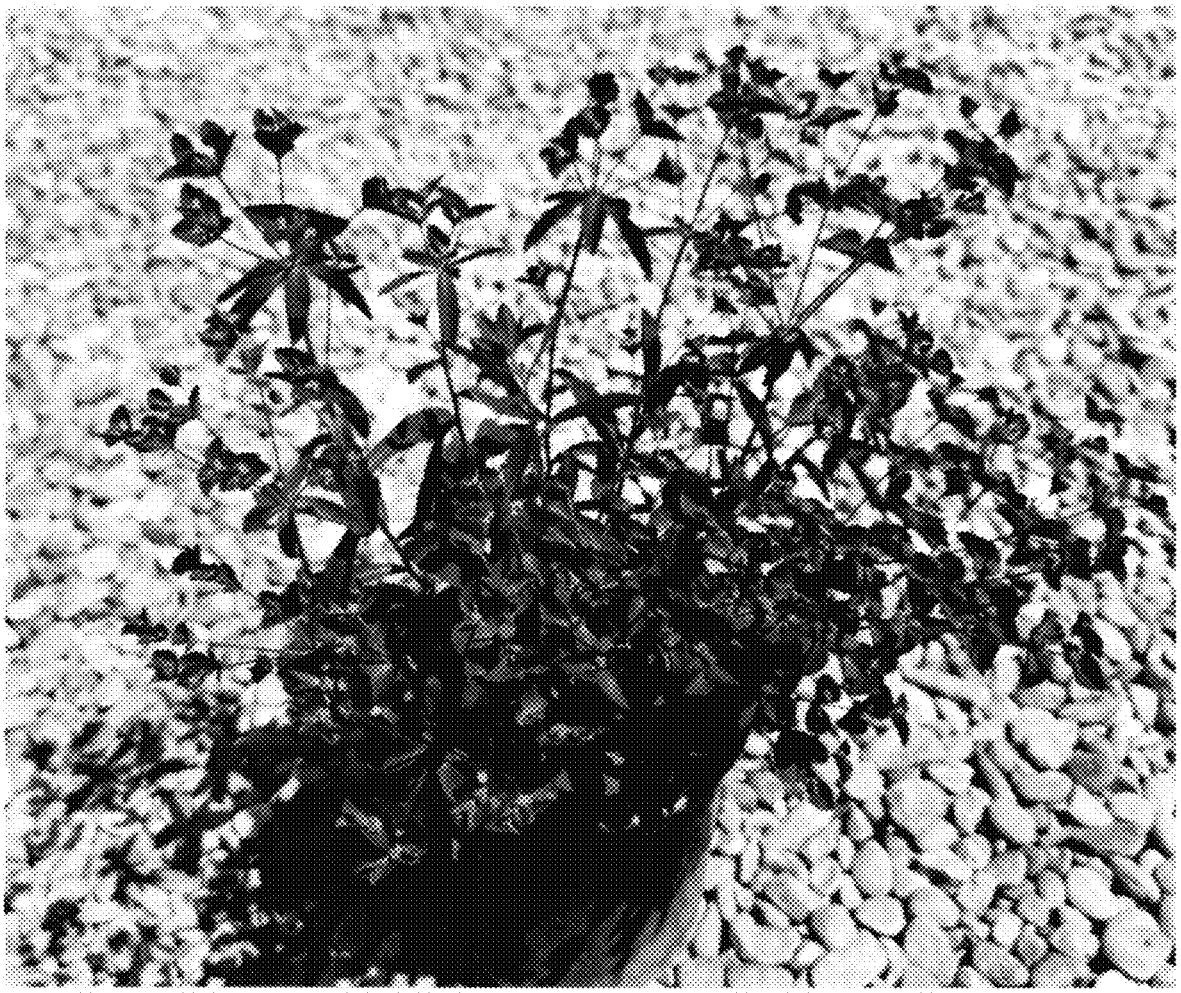
FIG. 1 provides a side view of the plant habit of 'Miner's Berry Bordeaux'.
Figure 2:
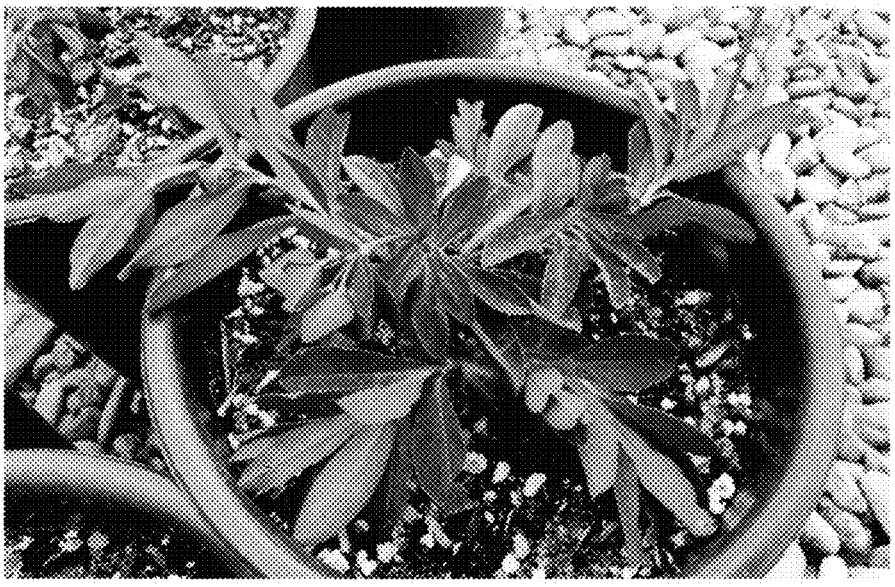

The photograph in FIG. 2 provides a view of the foliage color in fall of 'Miner's Berry Bordeaux'.

Figure 3:
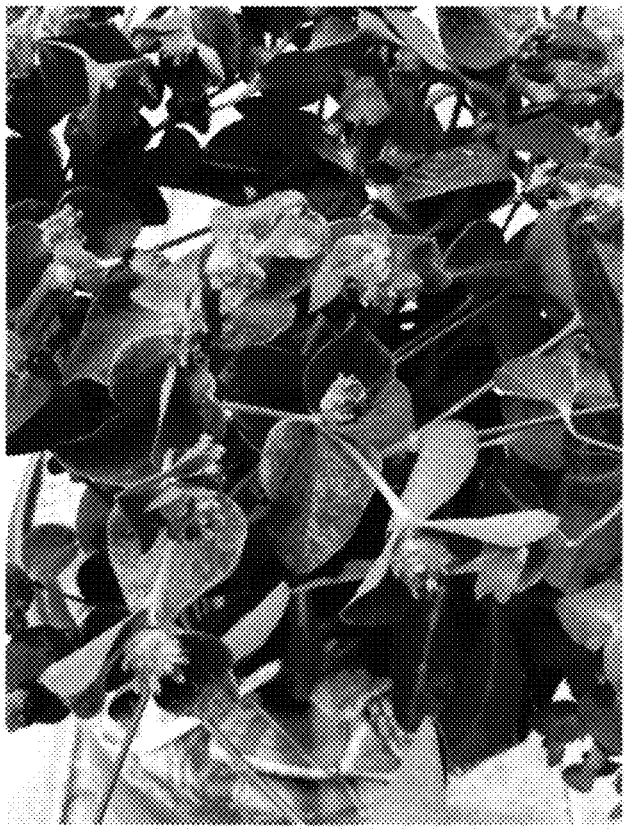

The photograph in FIG. 3 provides a close-up view of the inflorescences of 'Miner's Berry Bordeaux'.

Figure 4:
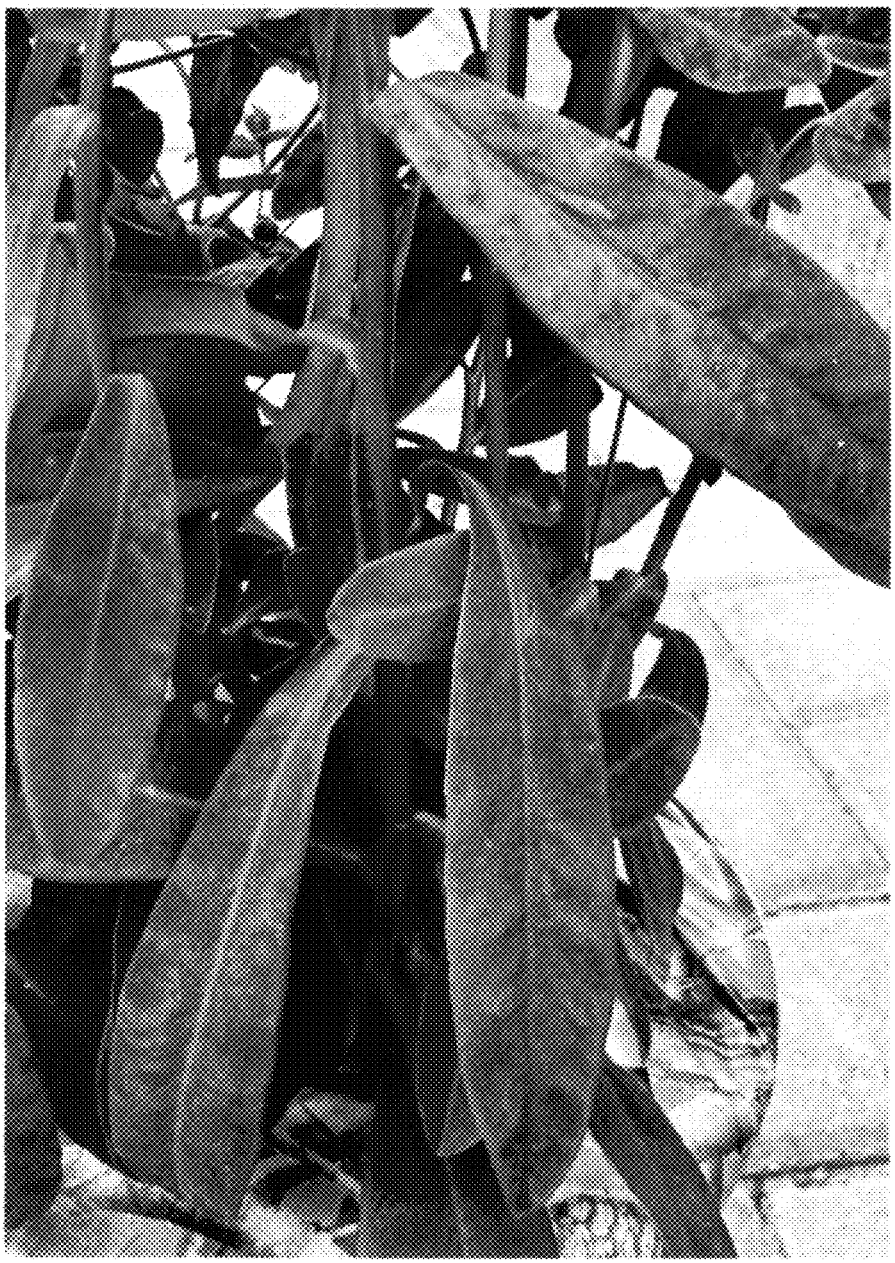

The photograph in FIG. 4 provides a close-up view of the summer foliage of 'Miner's Berry Bordeaux'.

The colors in the photographs are as close as possible with the photographic and printing technology utilized and the color values cited in the detailed botanical description accurately describe the colors of the new *Euphorbia*.

DETAILED BOTANICAL DESCRIPTION OF THE PLANT

The following is a detailed description of 9-month-old plants of the new cultivar as grown outdoors in one-gallon containers in Foresthill, California. The phenotype of the new cultivar may vary with variations in environmental, climatic, and cultural conditions, as it has not been tested under all possible environmental conditions. The color determination is in accordance with The 2015 Colour Chart of The Royal Horticultural Society, London, England, except where general color terms of ordinary dictionary significance are used.

General description:

*Blooming period*.—April through June in California.

*Plant type*.—Herbaceous perennial.

*Plant habit*.—Upright, compact.

*Height and spread*.—An average of 30 cm in height and 22 cm in width as a 9-month-old plant grown in a container, reaches an average of 46 cm in height and 61 cm in width as grown in the landscape.

*Cold hardiness*.—At least to U.S.D.A. Zone 4.

*Diseases and pests*.—No susceptibility or resistance to specific diseases or pests has been identified but plants have been observed to be disease free and has shown high deer resistance.

*Root description*.—Fine, fibrous, 155D in color.

*Root development*.—Average of 3 to 4 weeks to initiate roots and a young rooted plant in a 4-inch container is produced in about 4 weeks.

*Propagation type*.—Stem cuttings.

*Growth rate*.—Vigorous.

Branch description:

*Branch shape*.—Rounded.

*Branch color*.—Young and mature; ranging between 183A and 182A, in fall changing to 183A in color, before going dormant 182B in color.

*Branch size*.—Average of 12 cm in length, 5 mm in width.

*Branch surface*.—Glabrous, ranging between slightly glossy and matte.

*Branch aspect*.—Held in mutliple angles ranging between upright and outward.

*Branch strength*.—Flexible but strong.

*Internode length*.—An average of 5 cm at mid stem.

*Branching habit*.—Freely branching, 12 branches.

Foliage description:

*Leaf shape*.—Linear-oblanceolate.

*Leaf division*.—Simple.

*Leaf base*.—Attenuate to rounded.

*Leaf apex*.—Obtuse.

*Leaf venation*.—Pinnate, color matches surface colors.

*Leaf margins*.—Entire.

*Leaf attachment*.—Sessile.

*Leaf arrangement*.—Whorled to opposite.

*Leaf surface*.—Both surfaces matte.

*Leaf color* (*both surfaces*).—Young and mature; blend of 143B, 187A, and N186A, in fall changing to 183A in color, before going dormant 182B in color.

*Leaf size*.—Up to 4 cm in length and 1.5 cm in width.

Flower description:

*Inflorescence type*.—Umbel-like compound terminal cyme with single cymes on lower axils.

*Flower fragrance*.—None.

*Inflorescence longevity*.—Average of 14 days.

*Inflorescence size*.—12 cm in length, 10 cm in width with individual cymes an average of 2 cm in height and width.

*Flower type*.—Cyathium comprised of a cup-shaped involucre, a female flower and reduced male flowers, asepalous and apetalous.

*Cyathia quantity*.—Average of 30 per inflorescence.

*Cyathia aspect*.—Held in various angles, upward to outward to drooping.

*Cyathia size*.—An average of 1 cm in depth, 1.3 cm in diameter.

*Peduncles*.—An average of 5 per terminal compound cyme and 2 per axillary cymes, an average of 5 cm in length and 1.2 mm in diameter, surface is matte and glabrous, held upright, moderate strength, 187A in color, in fall changing to 183A in color, before going dormant 182B in color.

*Pedicels* (*stem of cyathia*).—An average of 1.5 cm in length and 1 mm in diameter, surface is matte and glabrous, held upright, moderate strength, 187A in color, in fall changing to 183A in color, before going dormant 182B in color.

*Nectaries*.—None.

*Floral bracts*.—2 opposite at base of cymes, cordate to deltoid in shape, 2.5 cm in length, 1.5 cm in width, rounded to slight cuspidate apex, fused base, both surfaces are glabrous and matte, entire margins, color; both surfaces when opening a blend of 143B, 187A, and N186A, center is a blend of 143B and 1C, both surfaces when fully open 187A, as it ages turning 187C, before dormancy 182C, terminal compound cyme; 4 in a whorl, 4 mm in length and 5 mm in width, both surfaces are glabrous and matte, obovate in shape, cuneate base, acute to bluntly acute apex, sometimes very small cuspidate tip, color; both surfaces when opening a blend of 143B, 187A and N186A, center is a blend of 143B and 1C, both surfaces when fully open 187A, as it ages turning 187C, color in fall until dormancy; upper surface a blend of 187B and N77B, lower surface a blend of 70B and 70C.

*Involucral bracts.*—4, surfaces are matte, color of both surfaces 180B, fading to 181C before dropping, 0.5 mm in length, 0.7 mm in width.

Reproductive organs:

*Gynoecium.*—One per central female flower (apetalous and asepalous), pistil; 3-parted with bifid, stigmas; 0.5 mm in length, 183A in color, style is minute, 0.3 mm in length, 183A in color, ovary; urn-shaped shape, 1 mm in length, NN155D in color.

*Androecium.*—An average of 4 reduced stamens, oval in shape and bi-lobed, 0.3 mm in length, 183A in color, no pollen was observed.

*Fruit/seed.*—Fruits; wart-like appearance, round to oval in shape, surface is rugose, 3 mm in diameter, young fruit color 143B, mature fruit color 181C, seeds; 4 per fruit, oval shaped, 1 mm in length and width, NN155D in color, surfaces are glabrous and matte.

It is claimed:

1. A new and distinct cultivar of *Euphorbia* plant named 'Miner's Berry Bordeaux' as herein illustrated and described.

* * * * *